US011891476B2

(12) United States Patent
Lal et al.

(10) Patent No.: US 11,891,476 B2
(45) Date of Patent: Feb. 6, 2024

(54) PHENALKAMINE EPOXY CURING AGENTS FROM METHYLENE BRIDGED POLY(CYCLOHEXYL-AROMATIC) AMINES AND EPOXY RESIN COMPOSITIONS CONTAINING THE SAME

(71) Applicant: Evonik Operations GmbH, Essen (DE)

(72) Inventors: Gauri Sankar Lal, Whitehall, PA (US); Michael Cook, Macungie, PA (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/076,866

(22) Filed: Oct. 22, 2020

(65) Prior Publication Data

US 2021/0139642 A1 May 13, 2021

Related U.S. Application Data

(60) Provisional application No. 62/933,024, filed on Nov. 8, 2019.

(51) Int. Cl.
| | | |
|---|---|---|
| *C08G 59/62* | (2006.01) | |
| *C08G 59/40* | (2006.01) | |
| *C08G 59/50* | (2006.01) | |
| *C09D 163/00* | (2006.01) | |

(52) U.S. Cl.
CPC ....... *C08G 59/623* (2013.01); *C08G 59/4014* (2013.01); *C08G 59/5033* (2013.01); *C09D 163/00* (2013.01)

(58) Field of Classification Search
CPC .............. C08G 59/4014; C08G 59/623; C08G 59/5033; C09D 163/00
USPC ......................................................... 525/490
See application file for complete search history.

(56) References Cited

U.S. PATENT DOCUMENTS

| | | | |
|---|---|---|---|
| 4,981,889 A | 1/1991 | Baba et al. | |
| 5,130,402 A | 7/1992 | Akiyama et al. | |
| 5,280,091 A * | 1/1994 | Dubowik | C08G 59/5026 528/122 |
| 6,262,148 B1 | 7/2001 | Cheng et al. | |
| 2010/0286345 A1 * | 11/2010 | Sato | C08G 59/5033 252/182.13 |
| 2017/0137562 A1 * | 5/2017 | Zheng | C08G 59/60 |
| 2017/0240691 A1 | 8/2017 | Zheng et al. | |

FOREIGN PATENT DOCUMENTS

| | | |
|---|---|---|
| CN | 103102506 A | 5/2013 |
| CN | 107663268 A | 2/2018 |
| EP | 0214495 A2 | 3/1987 |
| EP | 2108668 A1 | 10/2009 |
| EP | 3170849 A1 | 5/2017 |
| GB | 1529740 A | 10/1978 |
| WO | 2000001659 A1 | 1/2000 |
| WO | 2009080209 A1 | 7/2009 |
| WO | 2014067096 A1 | 5/2014 |
| WO | 2015085461 A1 | 6/2015 |
| WO | 2015153399 A1 | 10/2015 |
| WO | 2017140687 A1 | 8/2017 |

OTHER PUBLICATIONS

Antonio Greco et al.: "Use of cardanol derivaties as plasticizers for PVC : Cardanol dervived PVC plasticizers", Journal of vinyl and additive Technology, vol. 24, 2016, pp. E62-E70, XP55581996, US.
Emilie Darroman et al.: "New aromatic Amine based on cardanol giving new biobased epoxy Networks with cardanol: Amine functionalized cardanol for epoxy resins", European Journal of Lipid science and Technology, vol. 117, No. 2, Oct. 16, 2014, pp. 178-189, XP55599696.
European Search Report dated Mar. 26, 2021 corresponding to European Application No. 20203494.8 filed Oct. 23, 2020 (6 pages).

* cited by examiner

*Primary Examiner* — David T Karst
(74) *Attorney, Agent, or Firm* — Andrew H. Chung; Linda S. Li; Jason S. Ngui

(57) ABSTRACT

The present invention relates to a new structural class of phenalkamine, phenalkamine curing agent compositions, methods of making such phenalkamine, and methods of making such compositions. The phenalkamine curing agent compositions of the present invention can be prepared by reacting cardanol with an aldehyde compound and a mixture of methylene bridged poly(cycloaliphatic-aromatic)amines. These curing-agent compositions may be used to cure, harden, and/or crosslink an epoxy resin.

5 Claims, No Drawings

PHENALKAMINE EPOXY CURING AGENTS FROM METHYLENE BRIDGED POLY(CYCLOHEXYL-AROMATIC) AMINES AND EPOXY RESIN COMPOSITIONS CONTAINING THE SAME

This Application claims the benefit of U.S. Application No. 62/933,024, filed Nov. 8, 2019, the contents of which are hereby incorporated by reference in its entirety into this application.

BACKGROUND OF THE INVENTION

The Mannich reaction is based on the reaction of an aldehyde, such as formaldehyde, a phenolic compound and an amine. Various forms of phenolic compounds, amines and aldehydes are utilized in this reaction. The Mannich base products are particularly suitable for curing epoxy resins.

Phenalkamine curing agents are a class of Mannich bases obtained by reacting cardanol-a phenolic extract of cashew nutshell liquid, an aldehyde compound, such as formaldehyde, and an amine. Generally, they are produced from the reaction of one molar equivalent of cardanol with one to two molar equivalent of an aliphatic polyethylene polyamine and one to two molar equivalent of formaldehyde at 80-100° C. Aromatic polyamines are also suitable for this reaction.

The commercially available phenalkamines NC 541 and NC 540 available from Cardolite Inc. and Sunmide CX105 available from Evonik Corp. use ethylenediamine and diethylenetriamine as the amine sources. The Sunmide 1151 phenalkamine available from Evonik Corp. utilizes m-xylenediamine as the amine raw material.

Phenalkamines are good epoxy resin hardeners for room temperature or low temperature curing applications. In addition, they offer good chemical resistance, excellent water resistance, good compatibility with epoxy resins, low toxicity and good flexibility. As a result, they are used in marine, industrial maintenance and civil engineering applications.

GB Patent No. 1,529,740 describes phenalkamines as mixtures of poly(aminoalkylene) substituted phenols (structure below) prepared from cardanol with polyethylene polyamines and formaldehyde. In general, easy control of the molecular weight distribution of these products is not possible and hence they are mostly viscous liquids.

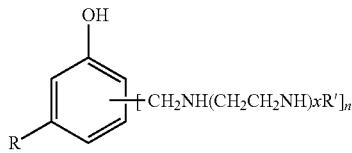

R=hydrocarbyl substituent with 15 carbon atoms, x=1-5, n=1-3, R'=H

U.S. Pat. No. 6,262,148 B1 describes compositions of phenalkamines bearing aromatic or alicyclic rings. These compositions were prepared from cardanol with aldehydes and alicyclic or aromatic polyamines. International Application Publication No. WO 2009/080209 A1 describes the preparation of epoxy curing agents comprising phenalkamines blended with polyamine salts. These curing agents were used to enhance the rate of cure of epoxy resins.

BRIEF SUMMARY OF THE INVENTION

This invention relates to phenalkamines which are obtained with a mixture of methylene bridged poly(cycloaliphatic-aromatic)amines (sometimes referred to as "MPCA") as the amine source. Consequently, the present disclosure discloses a new structural class of phenalkamine, curing agent compositions, methods of making such phenalkamine, and methods of making such compositions. These curing-agent compositions may be used to cure, harden, and/or crosslink an epoxy resin. In addition, these inventive phenalkamine curing agents can provide dry cure of epoxy coatings at ambient temperature (23° C.) in <8 h or at 5° C. in <16 h and provide improved coating performance as shown by enhanced low temperature surface appearance and improvements in chemical resistance. This combination of properties would allow for the further utilization of MPCA based phenalkamines as curing agents for low temperature tank linings where improved chemical resistance for transportation and storage of chemicals in the oil & gas sectors are required.

The inventive MPCA based phenalkamines, in comparison with the phenalkamines of the state of the art, have the advantage of providing a faster amine-epoxy reaction rate. This unique property provides the advantages of lower tendency to carbamate and shorter time for coatings to dry as compared to traditional phenalkamine products derived from alkylene amines such as ethylenediamine. In addition, coating compositions based on the MPCA phenalkamine curing agents of the present invention exhibit very good chemical resistance to a range of chemical reagents including alcohols (ethanol, methanol), xylenes, ketones (methyl isobutyl ketone), caustic soda and sulfuric acid and is superior in this respect to coatings made from phenalkamines derived from ethylenediamine.

In the preparation of the MPCA mixture, a condensation product of aniline or toluidine with formaldehyde containing substantial amounts of oligomer, is subjected to a catalytic hydrogenation process. The more volatile hydrogenated and partially hydrogenated products are separated by distillation and the heavier component (MPCA) or bottoms of the original mixture is thereby obtained. MPCA is represented by the chemical structure below:

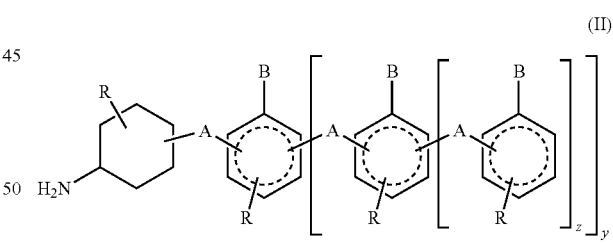

where R is independently of each other selected from H and $CH_3$;

is independently of each other selected from cyclohexyl and phenyl; A is independently of each other selected from $CH_2$ and NH; B is independently of each other selected from H, OH, and $NH_2$; y=0-1; z=0-1; and the sum of y and z is from 0 to 2.

The present invention relates to a phenalkamine mixture obtained by reacting cardanol (structure according to formula III below) with MPCA (structure according to formula II above) and an aldehyde to obtain the composition represented by the structure according to formula IV below. While formula IV shows the composition of the aldehyde and cardanol with one amino group of MPCA it is possible for the other amino groups of MPCA to react in a similar manner to generate a mixture of amine-substituted products.

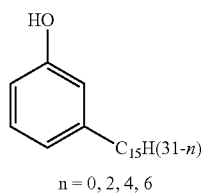

(III)

n = 0, 2, 4, 6

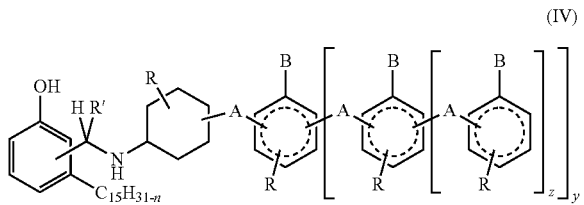

(IV)

where n=0, 2, 4, or 6; R is independently of each other selected from H and $CH_3$;

is independently of each other selected from cyclohexyl and phenyl; A is independently of each other selected from $CH_2$ and NH; B is independently of each other selected from H, OH, and $NH_2$; R'=H, $C_1$-$C_{10}$ alkyl, Ph, a $C_5$-$C_6$ cycloaliphatic group, or a $C_5$-$C_{10}$ aromatic group; y=0-1; z=0-1; and the sum of y and z is from 0 to 2. Preferably, R'=H or $C_1$ alkyl.

The present disclosure also provides for a curing agent composition comprising the phenalkamine mixture of formula (IV).

Preferable curing agent compositions of the present disclosure have an amine hydrogen equivalent weight (AHEW) based on 100% solids from about 50 to about 500. The present disclosure, in another aspect, provides amine-epoxy compositions and the cured products produced therefrom. For example, an amine-epoxy composition, in accordance with the present disclosure, comprises a curing agent composition containing the novel phenalkamine composition comprising at least one cardanol group and having at least two active amine hydrogen atoms and an epoxy composition comprising at least one multifunctional epoxy resin.

The present disclosure also provides for the use of a curing agent composition comprising the phenalkamine mixture of formula (IV) as a hardener for epoxy resins. Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds may be applied to metal or cementitious substrates. The mix of curing agent and epoxy resin often requires no "ripening time" for obtaining contact products with high gloss and clarity. Ripening time or incubation time is defined as the time between mixing epoxy resin with amine and applying the product onto the target substrate. It could also be defined as the time required for the mix to become clear.

DETAILED DESCRIPTION OF INVENTION

The novel phenalkamine mixture of the present invention can be prepared by reacting cardanol with an aldehyde compound and MPCA to produce the composition represented by the structure according to formula (IV) below:

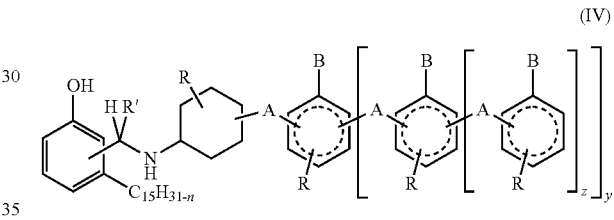

(IV)

where n=0, 2, 4, or 6; R is independently of each other selected from H and $CH_3$;

is independently of each other selected from cyclohexyl and phenyl; A is independently of each other selected from $CH_2$ and NH; B is independently of each other selected from H, OH, and $NH_2$; R'=H, $C_1$-$C_{10}$ alkyl, Ph, a $C_5$-$C_6$ cycloaliphatic group, or a $C_5$-$C_{10}$ aromatic group; y=0-1; z=0-1; and the sum of y and z is from 0 to 2. Preferably, R'=H or $C_1$ alkyl.

In a preferred embodiment, the phenalkamine mixture is represented by the structure according to formula (V) below:

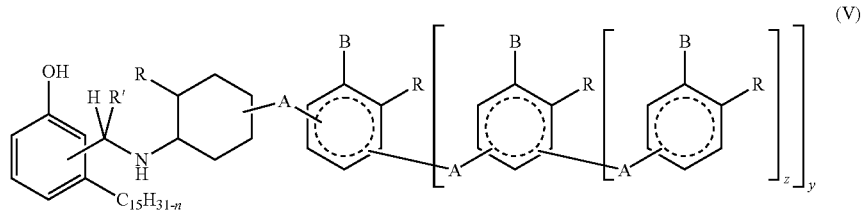

(V)

wherein n=0, 2, 4, or 6; R is independently of each other selected from H and CH$_3$;

is independently of each other selected from cyclohexyl and phenyl; A is independently of each other selected from CH$_2$ and NH; B is independently of each other selected from H, OH, and NH$_2$; R'=H, C$_1$-C$_{10}$ alkyl, Ph, a C$_5$-C$_6$ cycloaliphatic group, or a C$_5$-C$_{10}$ aromatic group; y=0-1; z=0-1; and the sum of y and z is from 0 to 2. Preferably, R'=H or C$_1$ alkyl.

In another preferred embodiment, the phenalkamine mixture is represented by the structure according to formula (VI) below:

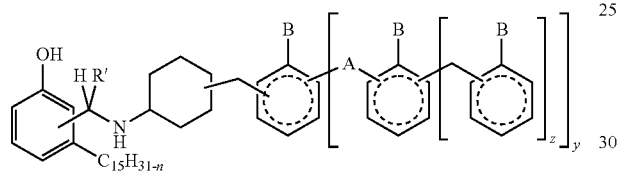
(VI)

wherein n=0, 2, 4, or 6;

is independently of each other selected from cyclohexyl and phenyl; A is independently of each other selected from CH$_2$ and NH; B is independently of each other selected from H, OH, and NH$_2$; R'=H, C$_1$-C$_{10}$ alkyl, Ph, a C$_5$-C$_6$ cycloaliphatic group, or a C$_5$-C$_{10}$ aromatic group; y=0-1; z=0-1; and the sum of y and z is from 0 to 2. Preferably, R'=H or C$_1$ alkyl.

Preferably, the phenalkamine mixture includes at least one phenalkamine selected from the following group

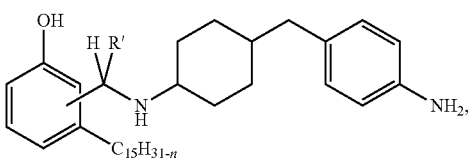
(VII)

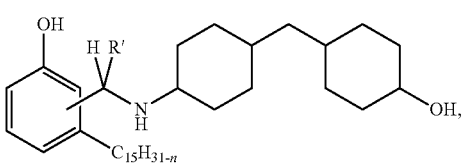
(VIII)

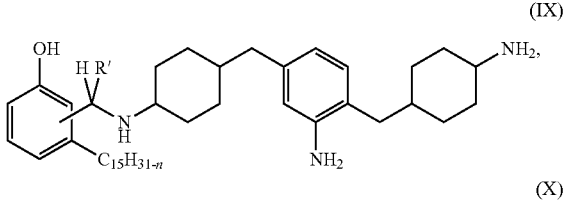
(IX)

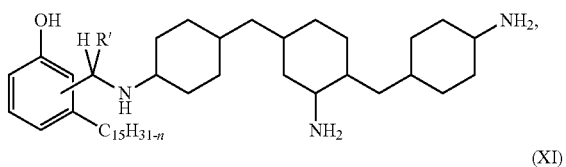
(X)

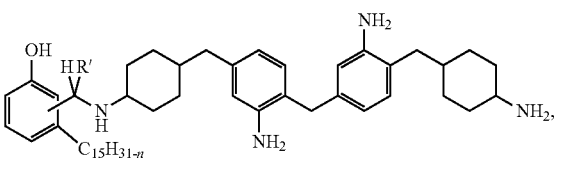
(XI)

and

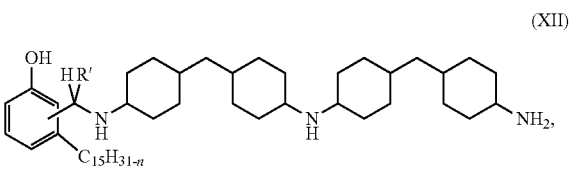
(XII)

wherein n=0, 2, 4, or 6; and R'=H, C$_1$-C$_{10}$ alkyl, Ph, a C$_5$-C$_6$ cycloaliphatic group, or a C$_5$-C$_{10}$ aromatic group. In a preferred embodiment, the phenalkamine mixture comprises each of the six phenalkamines listed in the above group. Preferably, in the curing agent composition comprising a phenalkamine mixture comprising six phenalkamines from the phenalkamines of formulas (VII), (VIII), (IX), (X), (XI) and (XII), the phenalkamines are present in the mixture as follows: 3-9 wt % phenalkamine of formula (VII), 3-11 wt % phenalkamine of formula (VIII), 30-45 wt % phenalkamine of formula (IX), 10-17 wt % phenalkamine of formula (X), 5-10 wt % phenalkamine of formula (XI), and 15-30 wt % phenalkamine of formula (XII). Preferably, R'=H or C$_1$ alkyl.

The present disclosure also provides for a curing agent composition comprising a phenalkamine mixture of any of formulas (IV), (V), or (VI). In a preferred embodiment, the curing agent composition comprises a phenalkamine mixture comprising at least one phenalkamine of formula (VII), (VIII), (IX), (X), (XI), or (XII). In another preferred embodiment, the curing agent composition comprises a phenalkamine mixture comprising six phenalkamines from the phenalkamines of formulas (VII), (VIII), (IX), (X), (XI) and (XII).

In a preferable embodiment, the curing agent composition may further include an additional amine having at least two amine functionalities. The phenalkamine curing agent of this invention may be used in combination with an additional amine curing agent (as a co-curing agent) for curing epoxy resins.

Preferable examples of additional amines having at least two amine functionalities include diethylenetriamine (DETA), triethylenetetramine (TETA), tetraethylenepentamine (TEPA), pentaethylenehexamine (PEHA), hexamethylenediamine (HMDA), 1,3-pentanediamine (DYTEK™ EP), 2-methyl-1,5-pentanediamine (DYTEK™A), triaminononane, N-(2-aminoethyl)-1, 3-propanediamine (N-Amine), N,N'-1,2-ethanediylbis-1,3-propanediamine (N₄-amine), or dipropylenetriamine; an arylaliphatic amine such as m-xylylenediamine (mXDA), or p-xylylenediamine; a cycloaliphatic amine such as 1,3-bis(aminomethyl)cyclohexylamine (1,3-BAC), isophorone diamine (IPDA), 4,4'-methylenebiscyclohexanamine, 1,2-diaminocyclohexylamine (DCHA), aminopropylcyclohexylamine (APCHA), a methylene bridged poly (cycloaliphatic-aromatic) amine such as MPCA, an aromatic amine such as m-phenylenediamine, diaminodiphenylmethane (DDM), or diaminodiphenylsulfone (DDS); a heterocyclic amine such as N-aminoethylpiperazine (NAEP), or 3,9-bis(3-aminopropyl)2,4,8, 10-tetraoxaspiro (5,5)undecane; a polyalkoxyamine where the alkoxy group can be an oxyethylene, oxypropylene, oxy-1,2-butylene, oxy-1,4-butylene or co-polymers thereof such as 4,7-dioxadecane-1,10-diamine, I-propanamine, 3,3'-(oxybis (2,1-ethanediyloxy))bis(diaminopropylateddiethylene glycol) (ANCAMINE1922A), poly(oxy(methyl-1, 2-ethanediyl)), α-(2-aminomethylethyl) ω-(2-aminomethylethoxy) (JEFFAMINE D 230, D-400), triethyleneglycoldiamine and oligomers (JEFFAMINEXTJ-504, JEFFAMINE XTJ-512), poly(oxy(methyl-1,2-ethanediyl)), α, α'-(oxydi-2, 1-ethanediyl)bis(ω-(aminomethylethoxy)) (JEFFAMINE XTJ-511), bis(3-aminopropyl)polytetrahydrofuran 350, bis (3-aminopropyl)polytetrahydrofuran 750, poly(oxy(methyl-1, 2-ethanediyl)), α-hydro-ω-(2-aminomethylethoxy)ether with 2-ethyl-2-(hydroxymethyl)-1, -propanediol (3:I) (JEFFAMINE T-403), and diaminopropyldiaminopropyl dipropylene glycol.

Other additional amines having at least two amine functionalities include amidoamine and polyamide curing agents. Polyamide curing agents are comprised of the reaction products of dimerized fatty acid (dimer acid) and polyethyleneamines, and usually a certain amount of monomeric fatty acid which helps to control molecular weight and viscosity. "Dimerized" or "dimer" or "polymerized" fatty acid refers, to polymerized acids obtained from unsaturated fatty acids. Common mono-functional unsaturated C-6 to C-20 fatty acids also employed in making polyamides include tall oil fatty acid (TOFA) or soya fatty acid or the like.

Other additional amines having at least two amine functionalities include phenalkamines and Mannich bases of phenolic compounds with amines and formaldehyde. The present disclosure also provides amine-epoxy compositions and the cured products produced therefrom. The latter comprises the reaction product of:

(a) a curing agent composition comprising the MPCA derived Mannich base of cardanol (phenalkamine) shown below:

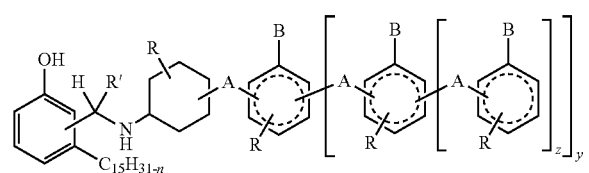

(IV)

where n=0, 2, 4, or 6; R is independently of each other selected from H and CH₃;

is independently of each other selected from cyclohexyl and phenyl; A is independently of each other selected from $CH_2$ and NH; B is independently of each other selected from H, OH, and $NH_2$; R'=H, $C_1$-$C_{10}$ alkyl, Ph, a $C_5$-$C_6$ cycloaliphatic group, or a $C_5$-$C_{10}$ aromatic group; y=0-1; z=0-1; and the sum of y and z is from 0 to 2; and (b) an epoxy composition comprising at least one multifunctional epoxy resin.

The present disclosure also provides for the use of a curing agent composition comprising a phenalkamine mixture of any of formulas (IV), (V) or (VI) as a hardener for epoxy resins. The present disclosure also provides for the use of a curing agent composition comprising a phenalkamine mixture comprising at least one phenalkamine of formula (VII), (VIII), (IX), (X), (XI), or (XII) as a hardener for epoxy resins. In a preferred embodiment, the curing agent composition comprises a phenalkamine mixture comprising at least six phenalkamines from the phenalkamines of formulas (VII), (VIII), (IX), (X), (XI) and (XII).

Amine-epoxy compositions of the present disclosure comprise a curing agent composition and an epoxy composition comprising at least one multifunctional epoxy resin. Multifunctional epoxy resin, as used herein, describes compounds containing 2 or more 1,2-epoxy groups per molecule. The epoxy resin is preferably selected from the group consisting of aromatic epoxy resin, alicyclic epoxy resin, aliphatic epoxy resin, glycidyl ester resin, thioglycidyl ether resin, N-glycidyl ether resin, and combinations thereof.

Preferable aromatic epoxy resin suitable for use in the present disclosure comprises the glycidyl ethers of polyhydric phenols, including the glycidyl ethers of dihydric phenols. Further preferred are the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present disclosure:

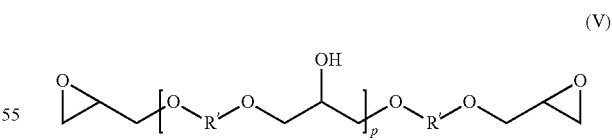

(V)

wherein R' is a divalent hydrocarbon radical of a dihydric phenol, such as those dihydric phenols listed above, and p is an average value between 0 and about 7. Materials according to this formula may be prepared by polymerizing mixtures of a dihydric phenol and epichlorohydrin, or by advancing a mixture of a diglycidyl ether of the dihydric phenol and the dihydric phenol. While in any given molecule the value of p is an integer, the materials are invariably mixtures which may be characterized by an average value of p which is not necessarily a whole number. Polymeric materials with an average value of p between 0 and about 7 may be used in one aspect of the present disclosure.

In one aspect of the present disclosure, the at least one multifunctional epoxy resin is preferably a diglycidyl ether of bisphenol-A (DGEBA), an advanced or higher molecular weight version of DGEBA, a diglycidyl ether of bisphenol-F, a diglycidyl ether of novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to about 3000 or more. Because these products are solid at room temperature, they are often referred to as solid epoxy resins.

In preferred embodiments, the at least one multifunctional epoxy resin is the diglycidyl ether of bisphenol-F or bisphenol-A represented by the following structure:

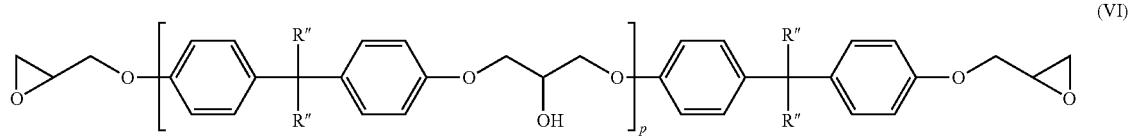

(VI)

wherein R"=H or $CH_3$, and p is an average value between 0 and about 7. DGEBA is represented by the above structure when R"=$CH_3$ and p=0. DGEBA or advanced DGEBA resins are often used in coating formulations due to a combination of their low cost and high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of about 174. Resins with EEWs between about 250 and about 450, also prepared by the advancement process, are referred to as semi-solid epoxy resins because they are a mixture of solid and liquid at room temperature. Multifunctional resins with EEWs based on solids of about 160 to about 750 are useful in the present disclosure. In another aspect the multifunctional epoxy resin has an EEW in a range from about 170 to about 250.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to, glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols, such as ethylene glycol, propylene glycol, trimethylol propane, and glycerin.

Glycidyl ester resins are obtained by reacting a polycarboxylic acid compound having at least two carboxyl acid groups in the molecule and epichlorohydrin. Examples of such polycarboxylic acids include aliphatic, cycloaliphatic, and aromatic polycarboxylic acids. Examples of aliphatic polycarboxylic acids include oxalic acid, succinic acid, glutaric acid, adipic acid, pimelic acid, sebacic acid, suberic acid, azelaic acid, or dimerised or trimerised linoleic acid. Cycloaliphatic polycarboxylic acids include tetrahydrophthalic acid, 4-methyltetrahydrophthalic acid, hexahydrophthalic acid or 4-methylhexahydrophthalic acid and aromatic polycarboxylic acids include phthalic acid, isophthalic acid or terephthalic acid.

Thioglycidyl ether resins are derived from dithiols, for example, ethane-1,2-dithiol or bis(4-mercaptomethylphenyl) ether.

N-glycidyl resins are obtained by dehydrochlorination of the reaction products of epichlorohydrin with amines containing at least two amine hydrogen atoms. Such amines are, for example, aniline, n-butylamine, bis(4-aminophenyl) methane, m-xylylenediamine or bis(4-methylaminophenyl) methane. The N-glycidyl resins also include, however, triglycidyl isocyanurate, N,N'-diglycidyl derivatives of cycloalkylene ureas, e.g., ethylene urea or 1,3-propylene urea, and diglycidyl derivatives of hydantoins, e.g., 5,5-dimethylhydantoin.

For one or more of the embodiments, the resin component further includes a reactive diluent. Reactive diluents are compounds that participate in a chemical reaction with the hardener component during the curing process and become incorporated into the cured composition, and are preferably monofunctional epoxides. Reactive diluents may also be used to vary the viscosity and/or cure properties of the curable compositions for various applications. For some applications, reactive diluents may impart a lower viscosity to influence flow properties, extend pot life and/or improve adhesion properties of the curable compositions. For example, the viscosity may be reduced to allow an increase in the level of pigment in a formulation or composition while still permitting easy application, or to allow the use of a higher molecular weight epoxy resin. Thus, it is within the scope of the present disclosure for the epoxy component, which comprises at least one multifunctional epoxy resin, to further comprise a monofunctional epoxide. Examples of monoepoxides include, but are not limited to, styrene oxide, cyclohexene oxide and the glycidyl ethers of phenol, cresols, tert-butylphenol, other alkyl phenols, butanol, 2-ethylhexanol, C4 to C14 alcohols, and the like, or combinations thereof. The multifunctional epoxy resin may also be present in a solution or emulsion, with the diluent being water, an organic solvent, or a mixture thereof. The amount of multifunctional epoxy resin may range from about 50% to 100%, about 50% to about 90%, about 60% to about 90%, about 70% to about 90%, and in some cases about 80% to about 90%, by weight, of the epoxy component. For one or more of the embodiments, the reactive diluent is less than 60 weight percent of a total weight of the resin component.

Particularly suitable multifunctional epoxy compounds are the diglycidyl ethers of bisphenol-A and bisphenol-F, the advanced diglycidyl ethers of bisphenol-A and bisphenol-F, and the epoxy novolac resins. The epoxy resin may be a single resin, or it may be a mixture of mutually compatible epoxy resins.

Amine-epoxy compositions of the present disclosure preferably have stoichiometric ratios of epoxy groups in the epoxy composition to amine hydrogens in the curing agent composition ranging from 1.5:1 to 0.7:1. For example, such amine-epoxy compositions may preferably have stoichiometric ratios of 1.5:1, 1.4:1, 1.3:1, 1.2:1, 1.1:1, 1:1, 0.9:1, 0.8:1, or 0.7:1. In another aspect, the stoichiometric ratio ranges from 1.3:1 to 0.7:1, or from 1.2:1 to 0.8:1, or from 1.1:1 to 0.9:1.

The combined MPCA derived Mannich base of cardanol (phenalkamine) and amine co-curing agent epoxy compositions of the present disclosure preferably have stoichiometric ratios of epoxy groups in the epoxy composition to amine hydrogens in the curing agent composition ranging from 1.5:1 to 0.7:1. For example, such amine-epoxy compositions may have stoichiometric ratios of 1.5:1, 1.4:1, 1.3:1, 1.2:1, 1.1:1, 1:1, 0.9:1, 0.8:1, or 0.7:1. In another aspect, the stoichiometric ratio ranges from 1.3:1 to 0.7:1, or from 1.2:1 to 0.8:1, or from 1.1:1 to 0.9:1.

Preferably, the weight ratio of the MPCA derived Mannich base of cardanol (phenalkamine) and amine co-curing agent is about 1:1 to about 1:0.05. In another embodiment, preferably the weight ratio of the MPCA-derived Mannich base of cardanol (phenalkamine) and amine co-curing agent is about 1:0.75 to about 1:0.25.

The present disclosure is also directed to a method for producing the phenalkamine mixture represented by any of formulas (IV), (V), or (VI) including the steps of reacting (i) cardanol represented by the formula

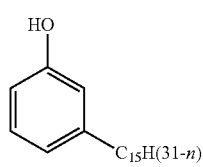

(III)

wherein n=0, 2, 4, or 6; (ii) MPCA represented by the formula

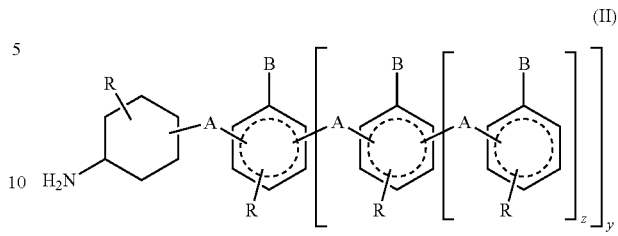

(II)

wherein R is independently of each other selected from H and $CH_3$;

is independently of each other selected from cyclohexyl and phenyl; A is independently of each other selected from $CH_2$ and NH; B is independently of each other selected from H, OH, and $NH_2$; y=0-1; z=0-1; and the sum of y and z is from 0 to 2; and (iii) an aldehyde.

In a preferred embodiment of the method, the mole ratio of cardanol to MPCA is within the range of from 1:1 to 1:3. In another embodiment, preferably the mole ratio of cardanol to MPCA is within the range of from 1:1 to 1:2. Preferably, the mole ratio of MPCA to aldehyde is within the range of from 1:1 to 1:3. In another embodiment, preferably the mole ratio of MPCA to aldehyde is within the range of from 1:1 to 1:1.2.

In a preferred embodiment of the method, the reaction can be carried out in a one-step process by mixing the cardanol with the amine and treating this mixture with formaldehyde at the desired reaction temperature. Alternately in another preferred embodiment of the method, the cardanol may preferably be mixed with the aldehyde and treated with the MPCA at the reaction temperature. The reaction may be carried out at 40° C.-150° C. In another preferable embodiment, the reaction may be carried out at 80° C.-120° C. The product is preferably obtained by distillation of water after the reaction is completed.

In a preferred embodiment of the method, the aldehyde compound used is represented by the structural formula RCOH, where R=H, $C_1$-$C_{10}$ alkyl, Ph, $C_5$-$C_6$ cycloaliphatic group, $C_5$-$C_{10}$ aromatic group or mixtures thereof. Preferable aldehydes are formaldehyde, acetaldehyde, propionaldehyde, butyraldehyde, pentanal, hexanal, heptanal, octanal, nonanal, decanal, benzaldehyde, cyclopentanecarboxaldehyde, and cyclohexanecarboxaldehyde. Most preferred aldehydes are formaldehyde and acetaldehyde. Formaldehyde can be used as an aqueous solution or in the polymeric form, paraformaldehyde.

The mole ratio of cardanol to MPCA and the aldehyde determines the extent of the reaction of the amino substituents in MPCA. Mixtures of amino substituents are expected. The ratio of higher substituted (>1) amine substituent on cardanol increases when the molar ratio of amino groups to cardanol is >1.0 assuming an equivalent molar ratio of amino groups to aldehyde.

The present disclosure is also directed to a method for producing a curing agent composition including the steps of combining a phenalkamine of any of formulas (IV), (V), or (VI) and an additional amine having at least two amine functionalities.

Compositions of the present disclosure may be used to produce various hardened articles of manufacture. Depending on the requirements during the manufacturing of or for the end-use application of the article, various additives may be employed in the formulations and compositions to tailor specific properties. These additives include, but are not limited to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art may be included in the compositions or formulations and are within the scope of the present disclosure.

The present disclosure is also directed to use of compositions of the present invention to prepare hardened articles of manufacture. For example, an article may comprise an amine-epoxy composition which comprises a curing agent composition and an epoxy composition. The curing agent composition may comprise the MPCA derived Mannich base of cardanol (phenalkamine). The epoxy composition may comprise at least one multifunctional epoxy resin. Optionally, various additives may be present in the compositions or formulations used to produce fabricated articles, dependent upon the desired properties. These additives may include, but are not limited to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof. The selection and amount of these additives is at the option of the formulator. Representative accelerators which may be used, although not mandatory include: boron trifluoride amine complexes, substituted phenols such as 2,4,6-tri(dimethylaminomethyl)phenol, tertiary amines such as benzyldimethylamine and imidazoles.

Preferred articles in accordance with the present disclosure include, but are not limited to, a coating, an adhesive, a primer, a sealant, a curing compound, a construction product, a flooring product, a composite product, laminate, potting compounds, grouts, fillers, cementitious grouts, or self-leveling flooring. Coatings based on these amine-epoxy compositions may contain diluents, such as water or organic solvents, as needed for the particular application. Coatings may contain various types and levels of pigments for use in paint and primer applications. Amine-epoxy coating compositions comprise a layer having a thickness ranging from 40 to 400 μm (micrometer), preferably 80 to 300 μm, more preferably 100 to 250 μm, for use in a protective coating applied onto metal substrates. In addition, for use in a flooring product or a construction product, coating compositions comprise a layer having a thickness ranging from 50 to 10,000 μm, depending on the type of product and the required end-properties. A coating product that delivers limited mechanical and chemical resistances comprises a layer having a thickness ranging from 50 to 500 μm, preferably 100 to 300 μm; whereas a coating product, such as, for example, a self-leveling floor that delivers high mechanical and chemical resistances comprises a layer having a thickness ranging from 1,000 to 10,000 μm, preferably 1,500 to 5,000 μm.

Additional components or additives may be used together with the compositions of the present disclosure to produce articles of manufacture. Further, such coatings, primers, sealants, curing compounds or grouts may be applied to metal or cementitious substrates.

The relative amount chosen for the epoxy composition versus that of the curing agent composition, may vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition may result in coatings which have increased drying time, but with increased hardness and improved appearance as measured by gloss.

Various substrates are suitable for the application of coatings of this invention with proper surface preparation, as is well known to one of ordinary skill in the art. Such substrates include, but are not limited to, concrete and various types of metals and alloys, such as steel and aluminum. Coatings of the present disclosure are suitable for the painting or coating of large metal objects or cementitious substrates including ships, bridges, industrial plants and equipment, and floors.

Coatings of this invention may be applied by any number of techniques including spray, brush, roller, paint mitt, and the like. In order to apply very high solids content or 100% solids coatings of this invention, plural component spray application equipment may be used, in which the amine and epoxy components are mixed in the lines leading to the spray gun, in the spray gun itself, or by mixing the two components together as they leave the spray gun. Using this technique may alleviate limitations with regard to the pot life of the formulation, which typically decreases as both the amine reactivity and the solids content increases. Heated plural component equipment may be employed to reduce the viscosity of the components, thereby improving ease of application.

Construction and flooring applications include compositions comprising the amine-epoxy compositions of the present disclosure in combination with concrete or other materials commonly used in the construction industry. Applications of compositions of the present disclosure include, but are not limited to, its use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present disclosure may be applied to surfaces to improve adhesive bonding prior to the application of a coating. As it pertains to concrete and cementitious application, a coating is an agent used for application on a surface to create a protective or decorative layer or a coat. Crack injection and crack filling products also may be prepared from the compositions disclosed herein. Amine-epoxy compositions of the present disclosure may be mixed with cementitious materials, such as concrete mix, to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the curing agent composition of the present disclosure, coatings may be applied to various substrates, such as concrete and metal surfaces at low temperature, with fast cure speed and good coating appearance. This is especially important for top-coat application where good aesthetics is desired, and provides a solution to a long-standing challenge in the industry where fast low-temperature cure with good coating appearance remains to be overcome. With fast low-temperature cure speed, the time service or equipment is down may be shortened, or for outdoor applications, the work season may be extended in cold climates.

Fast epoxy curing agents enable amine-cured epoxy coatings to cure in a short period of time with a high degree of cure. The cure speed of a coating is monitored by thin film set time (TFST) which measures the time period a coating dries. The thin film set time is categorized in 4 stages: phase 1, set to touch; phase 2, tack free: phase 3, dry hard; and phase 4, dry through. The phase 3 dry time is indicative of how fast a coating cures and dries. For a fast ambient cure coating, phase 3 dry time is less than 6 hours, or less than 4 hours, or preferred to be less than 4 hours. Low temperature cure typically refers to cure temperature below ambient temperature, 10° C. or 5° C., or 0° C. in some cases. For a fast low temperature cure, phase 3 dry time at 5° C. is less than 16 hours, with a significant productivity benefit being provided for values where phase 3 dry times are less than 10 hours and preferably less than 8 hours.

How well a coating cures is measured by the degree of cure. Degree of cure is often determined by using DSC (differential scanning calorimetry) technique which is well-known to those skilled in the art. A coating that cures thoroughly will have a degree of cure at ambient temperature (25° C.) of at least 85%, or at least 90%, or at least 95% after 7 days. A coating that cures thoroughly will have a degree of cure at 5° C. of at least 80%, or at least 85%, or at least 90% after 7 days.

Many of the fast low temperature epoxy curing agents may cure an epoxy resin fast. However due to poor compatibility of the epoxy resin and curing agents especially at low temperature of 10° C. or 5° C., there is phase separation between resin and curing agent and curing agent migrating to coating surface, resulting in poor coating appearance manifested as sticky and cloudy coatings. Good compatibility between epoxy resin and curing agent leads to clear glossy coating with good carbamation resistance and good coating appearance. The curing agent compositions of the present disclosure offers the combination of fast cure speed, good compatibility and high degree of cure.

EXAMPLES

These examples are provided to demonstrate certain aspects of the invention and shall not limit the scope of the claims appended hereto.

Example 1: Synthesis of the Phenalkamine of MPCA with Molar Ratio of Cardanol:MPCA:Formaldehyde (1:1:1)

A 3-neck 1 L round bottom flask equipped with $N_2$ inlet, addition funnel and temperature probe was charged with cardanol (298 g, 1.0 mole) and MPCA (350 g, 1.0 mole). The mixture was heated to 80° C. A 37% solution of formaldehyde (81 g, 37 wt. %, 30 g, 1.0 mole) was added to maintain a reaction temperature of 80-90° C. After the addition, the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (34.7 g) and benzyl alcohol (173 g). The resultant product had a viscosity of 5,710 mPa·s @ 23° C. and a theoretical AHEW of 150 g/eq.

Example 2: Synthesis of the Phenalkamine of MPCA with Molar Ratio of Cardanol:MPCA:Formaldehyde (1:1.5:1.0)

A 3-neck 1 L round bottom flask equipped with $N_2$ inlet, addition funnel and temperature probe was charged with cardanol (298 g, 1.0 mole) and MPCA (525 g, 1.50 mole). The mixture was heated to 80° C. A 37% solution of formaldehyde (81 g, 37 wt. %, 30 g, 1.0 mole) was added to maintain a reaction temperature of 80-90° C. After the addition the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (43.95 g) and benzyl alcohol (219.74 g). The resultant product had a viscosity of 6,290 mPa·s @ 23° C. and a theoretical AHEW of 154 g/eq.

Example 3: Synthesis of the Phenalkamine of MPCA with Molar Ratio of Cardanol:MPCA:Formaldehyde (1:1.5:1.25)

A 3-neck 1 L round bottom flask equipped with $N_2$ inlet, addition funnel and temperature probe was charged with cardanol (298 g, 1.0 mole) and MPCA (525 g, 1.50 mole). The mixture was heated to 80° C. A 37% solution of formaldehyde (101.35 g, 37 wt. %, 37.5 g, 1.25 mole) was added to maintain a reaction temperature of 80-90° C. After the addition, the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (44.10 g) and benzyl alcohol (220.5 g). The resultant product had a viscosity of 10,970 mPa·s @ 23° C. and a theoretical AHEW of 182 g/eq.

Example 4: Synthesis of the Phenalkamine of MPCA with Molar Ratio of Cardanol:MPCA:Aminopropyl Cyclohexylamine:Formaldehyde (1:0:0.8:0.2:1.0)

A 3-neck 1 L round bottom flask equipped with $N_2$ inlet, addition funnel and temperature probe was charged with cardanol (298 g, 1.0 mole), MPCA (280 g, 0.8 mole) and aminopropyl cyclohexylamine (31.25 g, 0.2 mole). The mixture was heated to 80° C. A 37% solution of formaldehyde (81 g, 37 wt. %, 30 g, 1.0 mole) was added to maintain a reaction temperature of 80-90° C. After the addition, the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (32.7 g) and benzyl alcohol (163.6 g). The resultant product had a viscosity of 2,440 mPa·s @ 23° C. and a theoretical AHEW of 233 g/eq.

Example 5: Synthesis of the Phenalkamine of MPCA with Molar Ratio of Cardanol:MPCA:Aminopropyl Cyclohexylamine:Formaldehyde (1:0:1.2:0.3:1.0)

A 3-neck 1 L round bottom flask equipped with $N_2$ inlet, addition funnel and temperature probe was charged with cardanol (298 g, 1.0 mole), MPCA (420 g, 1.2 mole) and aminopropyl cyclohexylamine (46.88 g, 0.3 mole). The mixture was heated to 80° C. A 37% solution of formaldehyde (81 g, 37 wt. %, 30 g, 1.0 mole) was added to maintain a reaction temperature of 80-90° C. After the addition, the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (40.9 g) and benzyl alcohol (204.5 g). The resultant product had a viscosity of 2,250 mPa·s @ 23° C. and a theoretical AHEW of 230 g/eq.

Example 6: Synthesis of the Phenalkamine of MPCA with Molar Ratio of Cardanol:MPCA:Triaminonane:Formaldehyde (1:0:0.65:0.65:1.3)

A 3-neck 1 L round bottom flask equipped with N₂ inlet, addition funnel and temperature probe was charged with cardanol (298 g, 1.0 mole), MPCA (227.5 g, 0.65 mole) and triaminononane (112.65 g, 0.65 mole). The mixture was heated to 80° C. A 37% solution of formaldehyde (105.4 g, 37 wt. %, 39 g, 1.3 mole) was added to maintain a reaction temperature of 80-90° C. After the addition, the mixture was kept at 90-95° C. for 1 h. Water was distilled at 120° C. and the product was obtained as a light brown liquid. This product was cooled to ambient temperature and treated with 2,4,6-tri(dimethylaminomethyl)phenol (34.41 g) and benzyl alcohol (172.03 g). The resultant product had viscosity of 2,100 mPa·s @ 23° C. and a theoretical AHEW of 136 g/eq.

Performance Testing

Curing agent mixtures were prepared by mixing the components given in the above examples. with the epoxy component of standard bisphenol-A based epoxy resin of (Epon 828, DER 331 type), EEW 190, unless specified otherwise. The formulations used are defined in Table 1. They were then mixed employing a stoichiometric level of 1:1 (amine:epoxy equivalents).

TABLE 1

| Clear Coat Formulation Screening - MPCA Phenalkamines | | | | | | | |
|---|---|---|---|---|---|---|---|
| Formulation | | Form [A] | Form [B] | Form [C] | Form [D] | Form [E] | Form [F] |
| Liquid BADGE Epoxy resin (EEW 190) | g | 100 | 100 | 100 | 100 | 100 | 100 |
| Example 1 | g | 90 | | | | | 80 |
| Example 2 | g | | 82.0 | | | | |
| Example 4 | g | | | 124.0 | | | |
| Example 6 | g | | | | 72.0 | | |
| Commercial [EDA] phenalkamine (AHEW 125) | g | | | | | 65.0 | |
| Anchor K54 | g | | | | | 3.4 | |
| Ancamine 2801 | g | | | | | | 5 |
| Total mix | g | 190 | 182 | 224 | 172 | 165 | 185 |

Form [E], the EDA based phenalkamine is the commercial product Sunmide ® CX105 (ex-Evonik). Anchor K54 was added to the formulation in order to achieve same accelerator level as present in all MPCA based formulations (Form [A]-[D])
Form [F] is an example of a blend of Example 1 with a fast co-amine crosslinker Ancamine ® 2801 (ex-Evonik)

Formulations as defined in Table 1, were subjected to a series of application tests to determine their performance attributes. The test protocols adapted are defined in Table 2.

TABLE 2

| Test Methods | | |
|---|---|---|
| Property | Response | Test Method |
| Gel time | 150 g sample (mins) | D2471 |
| Drying time: Beck-Koller (BK) recorder | Thin film set times phase III (h) | ASTM D5895 |
| Specular gloss | Gloss at 60° | ASTM D523 |
| Persoz pendulum hardness | Persoz hardness (s) | ASTM D4366 |
| Carbamation/Water spot resistance | Whitening of film after exposure to water droplet for 24 hrs @ 23° C. & 5° C. | Internal |
| Chemical resistance - Immersion | Weight gain after 7 days & 28 days continuous immersion | ASTM D543 |

The gel time characterizes the time a composition transitions from a liquid to a gel. The gel time of the amine-epoxy compositions was measured with TECHNE gelation timer model FGT 6 using ASTM D2471. The dry time or thin film set time (TFST) was determined using a Beck-Koller recorder, in accordance with ASTM D5895. The amine-epoxy coatings were prepared on standard glass panels at a wet film thickness of 150 μm WFT (wet film thickness) using a Bird applicator resulting in dry film thicknesses of ±100 μm. The coatings were cured at 23° C. and 5° C. and 60% relative humidity (RH) in a Lunaire (TPS) environmental chamber. The data for all the systems evaluated are reported in Table 3.

The results obtained clearly show that the coatings containing the curing agent of the present invention possess both fast cure and good coating appearance, indicative of good compatibility between curing agent and epoxy resin.

Many amine-based systems are prone to poor early water spot resistance and carbamation. The latter is where free amine present on the surface of a coating reacts with moisture and carbon dioxide in the atmosphere and the result is the formation of an insoluble white salt on the coating surface. In order to assess this, clear coatings were applied to clean Lenata charts at a wet film thickness of about 75 μm (wet film thickness) using a Bird applicator. The Lenata chart was cleaned with ethanol before use. The coatings were cured at 23° C. and 5° C. and 60% relative humidity

TABLE 3

Performance Properties of MPCA Phenalkamine Curing Agent

| Property | Conditions | Unit | Form [A] | Form [B] | Form [C] | Form [D] | Form [E] | Form [F] |
|---|---|---|---|---|---|---|---|---|
| Curing agent viscosity | 23° C. | mPa.s | 5,710 | 6,290 | 2,440 | 2,100 | 2,890 | 3,360 |
| Gel time | 23° C. | min | 59 | 64 | 64 | 58 | 68 | 53 |
| BK-TFST | 23° C. | h | 5.1 | 4.2 | 5.1 | 4.3 | 6.5 | 4.5 |
| (phase III) | 5° C./60% RH | h | 15.3 | 11.5 | 13.0 | 9.5 | 21.0 | 11.8 |
| Persoz Hardness | 23° C. | 1 d (s) | 227 | 238 | 304 | 297 | 86 | 305 |
|  |  | 7 d (s) | 335 | 339 | 339 | 330 | 285 | 337 |
| Coating appearance | 23° C. |  | Clear, glossy | Clear, glossy | Clear, glossy | Clear, glossy | Clear, sl haze | Clear, glossy |
|  | 5° C. |  | Clear, glossy | Clear, glossy | Clear, sl haze | Clear, glossy | hazy | Clear, glossy |
| Specular Gloss | 23° C. | 1 d | 112 | 115 | 110 | 109 | 100 | 111 |
| 60° | 5° C. |  | 106 | 108 | 93 | 105 | 72 | 108 |
| Water spot resistance | 23° C. | 1 d/7 d | 5/5 | 5/5 | 4/5 | 3/4 | 4/4 | 5/5 |
|  | 5° C. | 1 d/7 d | 5/5 | 5/5 | 3/4 | 3/4 | 1/3 | 4/5 |

The coatings compositions based on the curing agents of the present invention exhibit several improved properties vs those obtained with a standard commercially available EDA based phenalkamine when cured at both 23° C. and 5° C. These include a faster thin film dry time, hardness development and enhanced low temperature surface appearance, most noticeably when coatings are cured under adverse low temperature conditions. The results are deemed a significant performance benefit for these type of coatings as the faster property development and enhanced low temperature cure performance can provide productivity benefits in the marine and protective coating coatings market. Form [F] is an example where the addition of a second curing agent, to the new MPCA phenalkamine to form a co-mixture can also enhance performance properties. In this example, Ancamine 2801 curing agent at 5% lowers the initial curing agent viscosity shown by Example 1 by ±40% and in addition provides an improvement in the low temperature cure development without adversely impacting other properties such as the water spot resistance.

At 23° C. all coatings showed good gloss development and were free from any greasy amine and surface defects. At lower application temperatures the coatings based on MPCA maintained a very high gloss and grease free surface, whereas the reference phenalkamine used in Form [E] showed a decrease in the gloss and the clear coats developed a slight haze, which became more pronounced when this system was applied and cured at 5° C. The gloss and surface retention for formulations based on MPCA-phenalkamines developed from Examples 1, 2, and 6 were superior vs the EDA based control, which indicates improved compatibility for the curing agent technology based on the MPCA amine.

(RH) for 1 day and 7 days. A lint free cotton patch was placed on the test panel, ensuring that it is at least 12 mm from the edge of the panel. The cotton patch was dampened with 2-3 ml of de-mineralized water and covered with a suitable lid (e.g. watch glass). The panel was left undisturbed for the specified time (standard times is 24 h). After that time, the patch was removed and the coating was dried with a cloth or tissue. The panel was examined immediately for carbamation and rated. In the test used by Evonik a rating of 5 represents no carbamation and excellent surface, whereas 0 represents excessive whitening or severe carbamation. For water spot test a water droplet is applied to the coating, in the absence of the lint free cloth. The rating for water spot resistance is the same as for carbamation. The data, as summarized in Table 3, indicates that the coatings cured with the curing agents of the present invention provide improved carbamation and water spot resistance vs the reference phenalkamine, especially when applied at low temperature of 5° C.

Chemical Resistance Study

Several of the formulations based on the amine curing agents were also assessed for their base chemical resistance properties. In this test cured pucks with an approximate weight of 20.00 g (diameter ±55 mm, thickness ±10 mm) were prepared. Immersion studies following ASTM D543 were performed using standard liquid bisphenol-A based (DGEBA, EEW=190) epoxy resin cured with the curing agents from Example 1 for 7 days at 23° C. Two samples were tested for each reagent. Table 4 shows the average percentage weight change after immersion at 23° C. for 7 days, and 28 days in various chemicals.

TABLE 4

Chemical Resistance for MPCA-Phenalkamines - Continuous Immersion

| | Form [A] MPCA Phenalkamine | | Form [E] EDA Phenalkamine | |
|---|---|---|---|---|
| Reagent | 7 days % wt. change | 28 days % wt. change | 7 days % wt. change | 28 days % wt. change |
| Deionized Water | 0.58 | 0.74 | 0.41 | 0.88 |
| Methanol | 6.51 | 10.70 | 5.88 | 10.45 |
| Ethanol | 1.75 | 3.11 | 2.40 | 4.42 |
| Xylenes mixture | 0.33 | 0.82 | 26.2 | 44.41 |
| Methyl isobutyl ketone (MIBK) | 0.70 | 2.02 | 10.44 | 18.92 |
| 10% Caustic (NaOH) | 0.41 | 0.57 | 0.50 | 0.52 |
| 10% Sulfuric Acid ($H_2SO_4$) | 1.02 | 1.29 | 1.56 | 2.32 |

These studies show that the coating compositions based on the MPCA phenalkamine curing agents of the present invention exhibit very good chemical resistance to a range of chemical reagents. Most noticeably when compared to the standard EDA based phenalkamine is the superior resistance to xylene mixtures and methyl isobutyl ketone (MIBK). In this study pucks based on Form [A] exhibited very low levels of weight gain during immersion, whereas the EDA control showed several swelling and weight gains after 28 days immersion of 18.9% and 44.4% in MIBK and xylene respectively.

The invention claimed is:

1. A curing agent composition comprising a phenalkamine mixture comprising six phenalkamines of formulas (VII), (VIII), (IX), (X), (XI), and (XII):

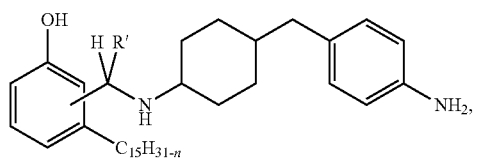
(VII)

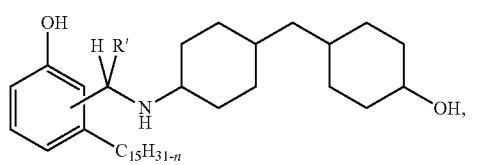
(VIII)

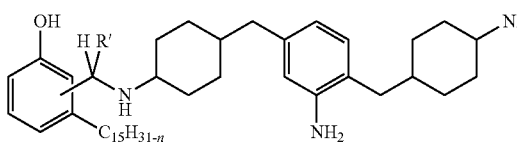
(IX)

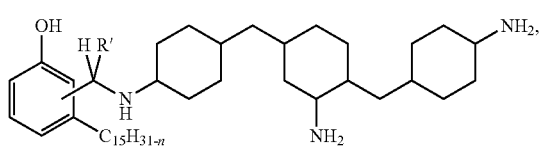
(X)

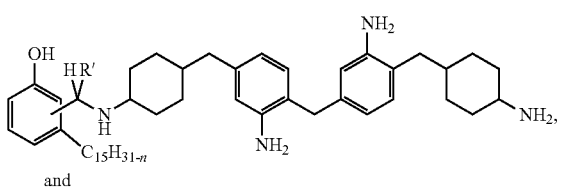
(XI)

and

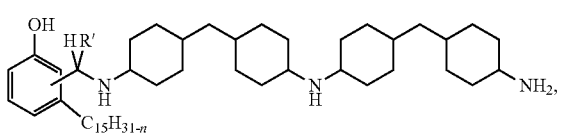
(XII)

wherein n=0, 2, 4, or 6; and R'=H, $C_1$-$C_{10}$ alkyl, Ph, a $C_5$-$C_6$ cycloaliphatic group, or a $C_5$-$C_{10}$ aromatic group and further comprising an additional amine having at least two amine functionalities selected from diethylenetriamine (DETA), triethylenetetramine (TETA), tetraethylenepentamine (TEPA), pentaethylenehexamine (PEHA), hexamethylenediamine (HMDA), 1,3-pentanediamine, 2-methyl-1,5-pentanediamine, triaminononane, N-(2-aminoethyl)-1,3-propanediamine ($N_3$-Amine), N,N'-1,2-ethanediylbis-1,3-propanediamine ($N_4$-amine), dipropylenetriamine; an arylaliphatic amine, m-xylylenediamine (mXDA), p-xylylenediamine, a cycloaliphatic amine, 1,3-bis(aminomethyl)cyclohexylamine (1,3-BAC), isophorone diamine (IPDA), 4,4'-methylenebiscyclohexanamine, 1,2-diaminocyclohexylamine (DCHA), aminopropylcyclohexylamine (APCHA), a methylene bridged poly (cycloaliphatic-aromatic) amine, an aromatic amine, m-phenylenediamine, diaminodiphenylmethane (DDM), diaminodiphenylsulfone (DDS); a polyalkoxyamine where the alkoxy group can be an oxyethylene, oxypropylene, oxy-1,2-butylene, oxy-1,4-butylene or co-polymers thereof, 4,7-dioxadecane-1,10-diamine, I-propanamine, 3,3'-(oxybis(2,1-ethanediyloxy))bis(diaminopropylated diethylene glycol), poly(oxy-(methyl-1,2-ethanediyl)), α-(2-aminomethylethyl) ω-(2-aminomethylethoxy), triethyleneglycoldiamine and oligomers, poly(oxy(methyl-1,2-ethanediyl)), αα'-(oxydi-2,1-ethanediyl)bis(ω-(aminomethylethoxy)), bis(3-amino-propyl) polytetrahydrofuran 350, bis(3-aminopropyl) polytetrahydrofuran 750, poly(oxy(methyl-1,2- ethanediyl)), α-hydro-ω-(2-aminomethylethoxy)ether with 2-ethyl-2-(hydroxymethyl)-1,3-propanediol (3:I), and diaminopropyldiaminopropyl dipropylene glycol, amidoamine and polyamide curing agents and Mannich bases of phenolic compounds with amines and formaldehyde.

2. An amine-epoxy composition comprising the reaction product of the curing agent composition according to claim 1 and an epoxy component.

3. An article of manufacture comprising the amine-epoxy composition as set forth in claim 2.

4. The article of manufacture of claim 3, wherein the article is a coating, an adhesive, a construction product, a flooring product, or a composite product.

5. A method for producing the curing agent composition of claim 1 comprising combining a phenalkamine mixture comprising six phenalkamines of formules (VII), (VIII), (IX), (X), (XI), and (XII):

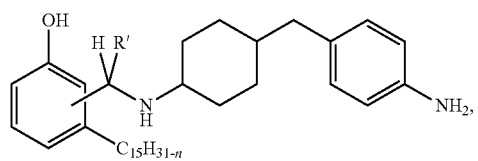
(VII)

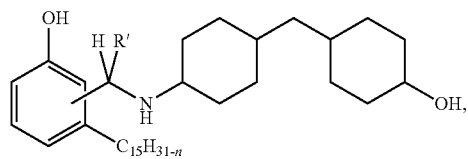
(VIII)

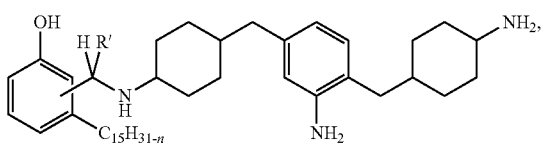
(IX)

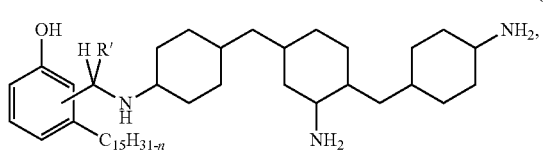
(X)

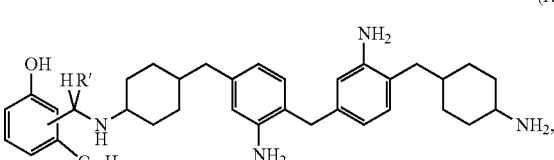
(XI)

and

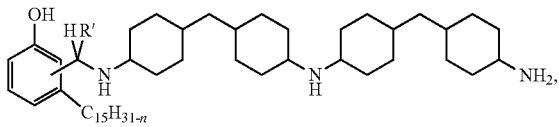
(XII)

wherein n=0, 2, 4, or 6; and R'=H, $C_1$-$C_{10}$ alkyl, Ph, a $C_5$-$C_6$ cycloaliphatic group, or a $C_5$-$C_{10}$ aromatic group and an additional amine having at least two amine functionalities selected from the group consisting of diethylenetriamine (DETA), triethylenetetramine (TETA), tetraethylenepentamine (TEPA), pentaethylenehexamine (PEHA), hexamethylenediamine (HMDA), 1,3-pentanediamine, 2-methyl-1,5-pentanediamine, triaminononane, N(2-aminoethyl)-1,3-propanediamine ($N_3$-Amine), N,N'-1,2-ethanediylbis-1,3-propanediamine ($N_4$-amine), dipropylenetriamine; an arylaliphatic amine, m-xylylenediamine (mXDA), p-xylylenediamine, a cycloaliphatic amine, 1,3-bis (aminomethyl)cyclohexylamine (1,3-BAC), isophorone diamine (IPDA), 4,4'-methylenebiscyclohexanamine, 1,2-diaminocyclohexylamine (DCHA), aminopropylcyclohexylamine (APCHA), a methylene bridged poly (cycloaliphatic-aromatic) amine, an aromatic amine, m-phenylenediamine, diaminodiphenylmethane (DDM), diaminodiphenylsulfone (DDS); a polyalkoxyamine where the alkoxy group can be an oxyethylene, oxypropylene, oxy-1,2-butylene, oxy-1, 4-butylene or co-polymers thereof, 4,7-dioxadecane-1, 10-diamine, I-propanamine, 3,3'-(oxybix(2,1-ethanediyloxy))bis(diaminopropylated diethylene glycol), poly(oxy(methyl-1,2-ethanediyl)), α(2-aminomethylethyl) ω(2-aminomethylethoxy), triethyleneglycoldiamine and oligomers, poly(oxy(methyl-1,2-ethanediyl), α,α'-(oxydi-2,1-ethanediyl)bis(ω-(aminomethylethoxy)), bis(3-aminopropyl) polytetrahydrofuran 350, bis(3-aminopropyl) polytetrahydrofuran 750, poly(oxy(methyl-1,2-ethanediyl)), α-hydro-ω-(2-aminomethylethoxy)ether with 2-ethyl-2-(hydroxymethyl)-1,3-propanediol (3:I), and diaminopropyldiaminopropyl dipropylene glycol, amidoamine and polyamide curing agents and Mannich bases of phenolic compounds with amines and formaldehyde.

* * * * *